(12) United States Patent
Mori et al.

(10) Patent No.: US 8,241,205 B2
(45) Date of Patent: Aug. 14, 2012

(54) ELECTRONIC ENDOSCOPE APPARATUS AND ELECTRONIC ENDOSCOPE SYSTEM

(75) Inventors: Takeshi Mori, Machida (JP); Hatsuo Shimizu, Hachioji (JP); Aiko Yoshida, Hino (JP)

(73) Assignee: Olympus Corporation, Tokyo (JP)

( * ) Notice: Subject to any disclaimer, the term of this patent is extended or adjusted under 35 U.S.C. 154(b) by 1273 days.

(21) Appl. No.: 11/890,620

(22) Filed: Aug. 7, 2007

(65) Prior Publication Data

US 2008/0039686 A1 Feb. 14, 2008

(30) Foreign Application Priority Data

Aug. 10, 2006 (JP) .................................. 2006-218508

(51) Int. Cl.
*A61B 1/04* (2006.01)
*A61B 1/06* (2006.01)
(52) U.S. Cl. ........................................ 600/109; 600/160
(58) Field of Classification Search ................... 600/103, 600/109, 160, 110; 348/65
See application file for complete search history.

(56) References Cited

U.S. PATENT DOCUMENTS

| | | | | |
|---|---|---|---|---|
| 4,473,841 A * | 9/1984 | Murakoshi et al. | ............. | 348/65 |
| 4,565,423 A * | 1/1986 | Ueda | ............................ | 359/503 |
| 4,802,018 A * | 1/1989 | Tanikawa et al. | ............. | 386/200 |
| 5,022,383 A * | 6/1991 | Sakiyama et al. | ............. | 600/109 |
| 5,074,642 A * | 12/1991 | Hicks | ............................ | 385/116 |
| 5,592,216 A * | 1/1997 | Uehara et al. | ................... | 348/74 |
| 5,910,816 A * | 6/1999 | Fontenot et al. | ................ | 348/65 |
| 6,677,984 B2 * | 1/2004 | Kobayashi et al. | ............. | 348/65 |
| 6,686,949 B2 * | 2/2004 | Kobayashi et al. | ............. | 348/65 |
| 6,690,409 B1 * | 2/2004 | Takahashi | ........................ | 348/65 |
| 6,753,901 B1 * | 6/2004 | Takahashi et al. | ............. | 348/65 |
| 7,591,783 B2 * | 9/2009 | Boulais et al. | ................ | 600/142 |
| 2002/0196335 A1 * | 12/2002 | Ozawa | ............................ | 348/70 |
| 2003/0219201 A1 * | 11/2003 | Arimoto et al. | ................ | 385/31 |
| 2004/0196364 A1 * | 10/2004 | Takahashi | ........................ | 348/65 |
| 2005/0277810 A1 * | 12/2005 | Irion | ............................ | 600/178 |
| 2007/0083083 A1 * | 4/2007 | Mori et al. | ...................... | 600/118 |
| 2007/0232860 A1 * | 10/2007 | Kubo et al. | ..................... | 600/160 |
| 2008/0116093 A1 * | 5/2008 | Felten et al. | ............... | 206/316.2 |

FOREIGN PATENT DOCUMENTS

JP 60-209717 A 10/1985

(Continued)

OTHER PUBLICATIONS

Japanese Office Action mailed Dec. 6, 2011 in corresponding Japanese Patent Application No. 2006218508 together with a partial English language translation.
Japanese Office Action mailed May 22, 2012 in corresponding Japanese Patent Application No. 2006-218508 together with a partial English language translation.

(Continued)

*Primary Examiner* — Philip R Smith
*Assistant Examiner* — William Chou
(74) *Attorney, Agent, or Firm* — Scully, Scott, Murphy & Presser, P.C.

(57) ABSTRACT

An electronic endoscope apparatus has a distal part, an imaging unit, a light emitting unit, and a transmitting unit. The imaging unit converts light applied to the distal part, into an electrical signal. The light emitting unit converts the electrical signal supplied from the imaging unit, into an optical signal. The transmitting unit, which is attached to the distal part, guides the optical signal supplied from the light emitting unit. The electrical signal output from the imaging unit is converted into an optical signal. This optical signal is transmitted from the distal part through the transmitting unit.

9 Claims, 7 Drawing Sheets

FOREIGN PATENT DOCUMENTS

| | | |
|---|---|---|
| JP | 1-280440 A | 11/1989 |
| JP | 6-34890 A | 2/1994 |
| JP | 3615890 | 11/2004 |
| JP | 2005-527253 | 9/2005 |
| JP | 2006-181021 A | 7/2006 |

OTHER PUBLICATIONS

English language abstract only of International Publication No. WO 03/030727 A2.

* cited by examiner

Video signal superposed with sync signal

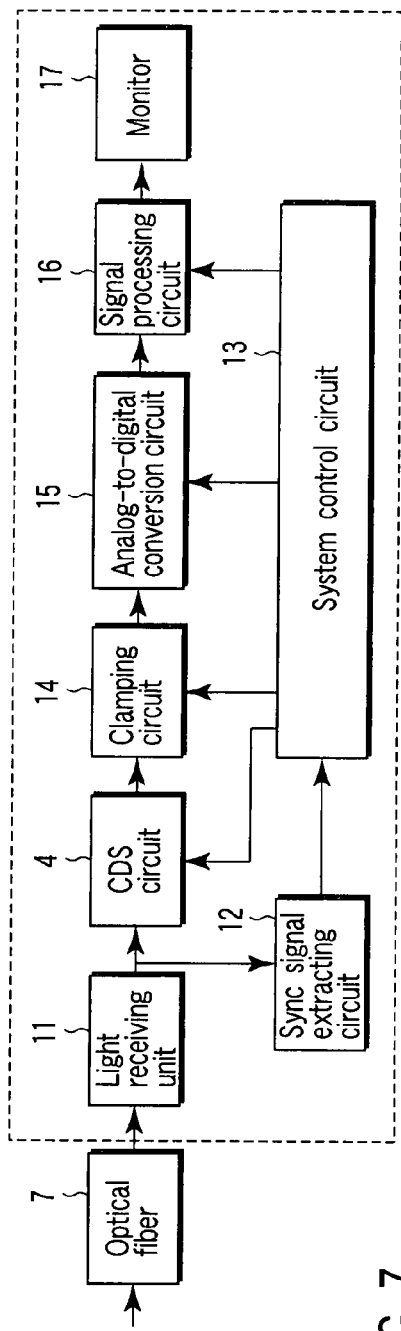
F I G. 7
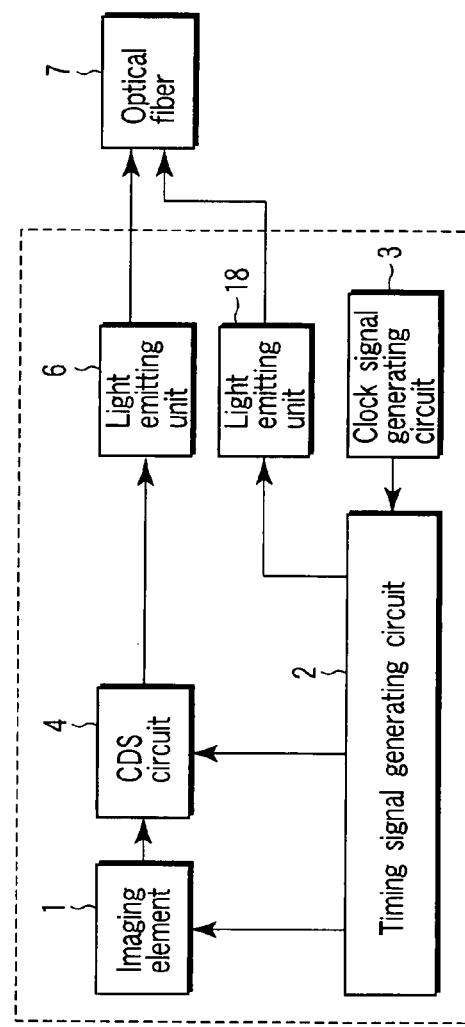
F I G. 8

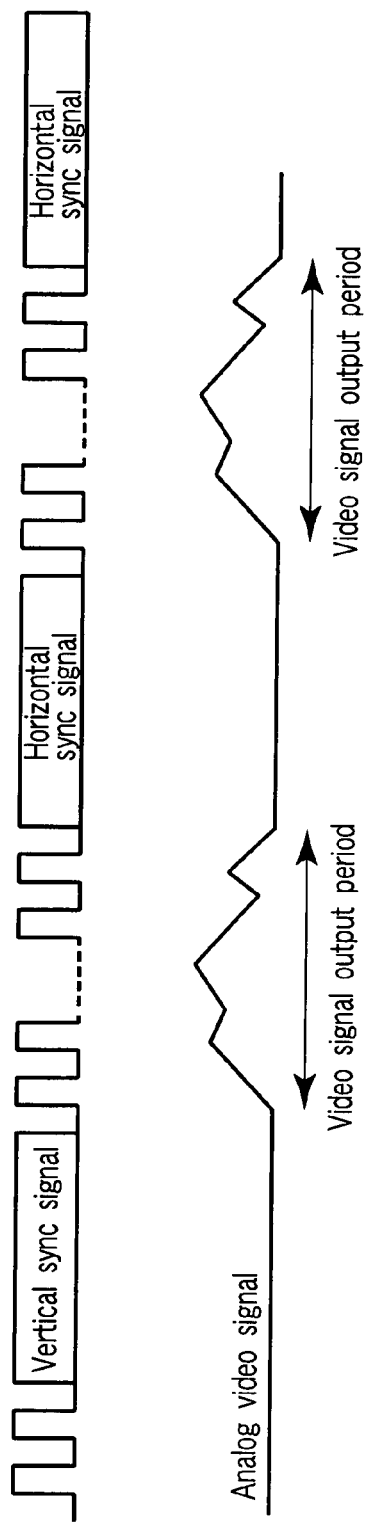
F I G. 9A
F I G. 9B
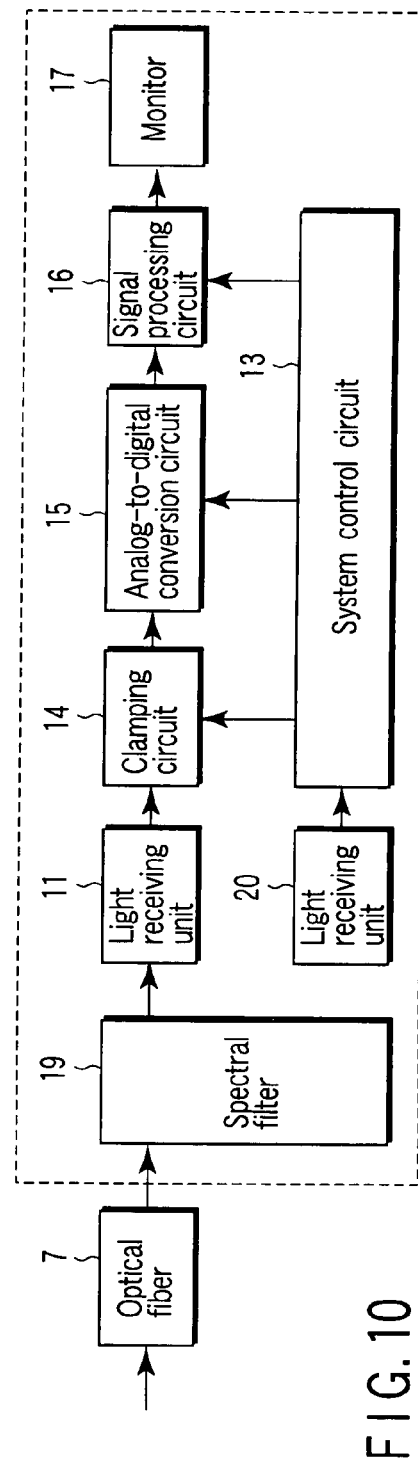
F I G. 10

ELECTRONIC ENDOSCOPE APPARATUS AND ELECTRONIC ENDOSCOPE SYSTEM

CROSS-REFERENCE TO RELATED APPLICATIONS

This application is based upon and claims the benefit of priority from prior Japanese Patent Application No. 2006-218508, filed Aug. 10, 2006, the entire contents of which are incorporated herein by reference.

BACKGROUND OF THE INVENTION

1. Field of the Invention

The present invention relates to an electronic endoscope apparatus and an electronic endoscope system. More particularly, the invention relates to a signal transmitting technique for use in an electronic endoscope apparatus and in an electronic endoscope system.

2. Description of the Related Art

Japanese Patent No. 3615890, for example, discloses an electronic endoscope apparatus, in which an optical interface accomplishes non-contact connection in signal transmission. Owing to the non-contact connection, no electrodes are exposed outside the electronic endoscope apparatus. The electronic endoscope can therefore be washed and sterilized, without being covered with a waterproof cap or the like. Further, since the electronic endoscope apparatus has no contacts, it can remain electrically isolate, which ensures safety to the patient.

The specification of Japanese Patent No. 3615890 describes nothing about the wiring provided in the main unit of the electronic endoscope apparatus. In one embodiment of the electronic endoscope apparatus, the components other than the optical element (i.e., imaging element), such as the digital processing circuit (DSP), are arranged together near the optical interface that connects the electronic endoscope apparatus to an external apparatus. In another embodiment of the electronic endoscope apparatus, the circuit section is arranged in the operation section.

BRIEF SUMMARY OF THE INVENTION

According to a first aspect of the present invention, there is provided an electronic endoscope apparatus comprising: a distal part; an imaging unit which is provided in the distal part and configured to convert light applied to the distal part, into an electrical signal; a light emitting unit which is configured to convert the electrical signal supplied from the imaging unit, into an optical signal; a transmitting unit which is attached to the distal part and configured to guide the optical signal from the light emitting unit, wherein the electrical signal supplied from the imaging unit is converted into an electrical signal, and the electrical signal is transmitted from the distal part through the transmitting unit.

According to a second aspect of the present invention, there is provided an electronic endoscope apparatus comprising: a distal part; an imaging unit which is provided in the distal part and configured to convert light applied to the distal part, into an electrical signal; a sampling unit which is configured to sample the electrical signal supplied from the imaging unit; a light emitting unit which is configured to convert a signal output from the sampling unit, into an optical signal; and a transmitting unit which is attached to the distal part and configured to guide the optical signal from the light emitting unit, wherein a baseband electrical signal supplied from the sampling unit is converted into an optical signal, and the optical signal is transmitted from the distal part through the transmitting unit.

According to a third aspect of the present invention, there is provided an electronic endoscope system comprising: an electronic endoscope apparatus including: an imaging unit which is configured to convert light into an electrical signal; a sampling unit which is configured to sample the electrical signal supplied from the imaging unit; a sync signal superposing unit which is configured to superpose a sync signal on a signal output from the sampling unit in order to reproduce an image; a light emitting unit which is configured to convert a signal output from the sync signal superposing unit, into an optical signal; and a transmitting unit which is configured to guide the optical signal from the light emitting unit, and an external apparatus including: a light receiving unit which is configured to convert the optical signal guided by the transmitting unit, into an electrical signal; a sync signal extracting unit which is configured to extract the sync signal from the electrical signal supplied from the light receiving unit; a control unit which is configured to generate a control signal for controlling any other component of the external apparatus; a display system; a signal processing unit which is configured to process the electrical signal supplied from the light receiving unit, thereby enabling the display system to display an image, wherein a baseband electrical signal supplied from the sampling unit is converted into an optical signal, and the optical signal is transmitted from the distal part through the transmitting unit.

According to a fourth aspect of the present invention, there is provided an electronic endoscope system comprising: an imaging unit which is configured to convert light into an electrical signal; a sampling unit which is configured to sample the electrical signal supplied from the imaging unit; a first light emitting unit which is configured to convert a signal output from the sampling unit, into an optical signal; at least one second light emitting unit which is configured to convert data different from the data contained in the optical signal generated by the first light emitting unit, into an optical signal having a wavelength different from that of the optical signal generated by the first emitting unit; a transmitting unit which is configured to multiplex the optical signals supplied from the first light emitting unit and the said at least one second light emitting units; a light splitting unit which is configured to split the optical signal supplied from the transmitting unit, into the optical signal supplied from the first light emitting unit and the optical signal supplied from the at least one second light emitting unit; a first light receiving unit which is configured to convert an optical signal equivalent to the optical signal supplied first from the first light emitting and then from the light splitting unit, into an electrical signal; a second light receiving unit which is configured to convert an optical signal equivalent to the optical signal supplied first from the at least one second light emitting and then from the light splitting unit, into an electrical signal; a signal processing unit which is configured to process the electrical signal output from the first light receiving unit; a display unit which is configured to display an image represented by the electrical signal output from the signal processing unit.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 7 is a block diagram showing the configuration of the external apparatus incorporated in the electronic endoscope system according to the second embodiment of the invention;

FIG. 8 is a block diagram showing the configuration of the electronic endoscope apparatus incorporated in an electronic endoscope system according to a third embodiment of the present invention;

FIG. 9A is a diagram representing the waveform of a sync signal to be multiplexed;

FIG. 9B is a diagram representing the waveform of a video signal to be multiplexed;

FIG. 10 is a block diagram showing the configuration of the external apparatus incorporated in the electronic endoscope system according to the third embodiment of the invention;

DETAILED DESCRIPTION OF THE INVENTION

Embodiments of the present invention will be described, with reference to the accompanying drawings.

First Embodiment

The first embodiment of the invention will be described. An electronic endoscope system according to the first embodiment is composed of an electronic endoscope apparatus and an external apparatus. In the electronic endoscope system, the electronic endoscope apparatus photographs the interior of the subject's body and generates a video signal representing the image of the interior of the body. The video signal is transmitted, as an optical signal, to the external apparatus. The external apparatus converts the optical signal into an electrical signal and displays the image represented by the electrical signal.

Figure 1:
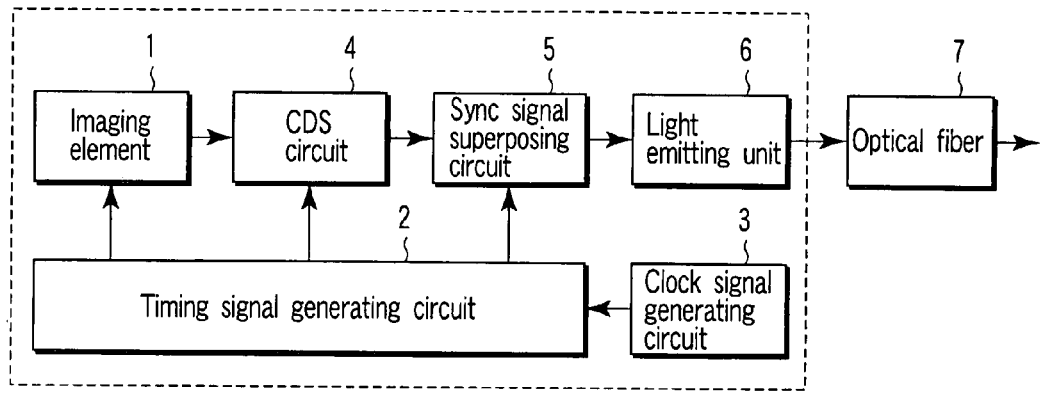
FIG. 1 is a block diagram showing the configuration of the electronic endoscope apparatus incorporated in an electronic endoscope system according to a first embodiment of the present invention.

FIG. 1 is a block diagram that shows the configuration of the electronic endoscope apparatus incorporated in the electronic endoscope system according to the first embodiment. The distal part of the electronic endoscope apparatus shown in FIG. 1 incorporates an imaging element 1, a timing signal generating circuit 2, a clock signal generating circuit 3, a correlated duplex sampling (CDS) circuit 4, a sync signal superposing circuit 5, and a light emitting unit 6. The distal part of the electronic endoscope apparatus is connected to an optical fiber 7.

The imaging element 1 receives light reflected from the interior of the subject's body cavity. The imaging element 1 converts the light into an electrical signal (i.e., a video signal), which is output to the CDS circuit 4. The timing signal generating circuit 2 receives a clock signal from the clock signal generating circuit 3 and generates drive pulses and sampling pulses. The drive pulses are supplied to the imaging element 1, driving the imaging element 1. The sampling pulses are supplied to the CDS circuit 4, designating sampling timing for the CDS circuit 4. The CDS circuit 4 samples the video signal coming from the imaging element 1, in synchronism with the sampling pulses. Signals sampled in the CDS circuit 4 are input to the sync signal superposing circuit 5. The sync signal superposing circuit 5 superposes a sync signal on the video signal output from the CDS circuit 4 so that the external apparatus may display the image. The light emitting unit 6 comprises a light emitting element, such as an LED, and a drive circuit for driving the light emitting element. The light emitting unit 6 converts the video signal superposed with the sync signal in the sync signal superposing circuit 5, into an optical signal. The optical signal is transmitted to the external apparatus through the optical fiber 7.

In the first embodiment, the video signal is transmitted from the imaging element 1, without being modulated, in an analog baseband signal. Therefore, the circuit configuration in the distal part of the electronic endoscope apparatus only needs an analog signal processing circuit, such as CDS circuit 4, and a drive circuit for the imaging element 1, such as the timing signal generating circuit 2. That is, since the distal part of the electronic endoscope apparatus need not have a digital signal processing circuit such as an analog-to-digital converter, only absolutely necessary components are provided. This helps to miniaturize the distal part of the electronic endoscope apparatus.

Figure 2:
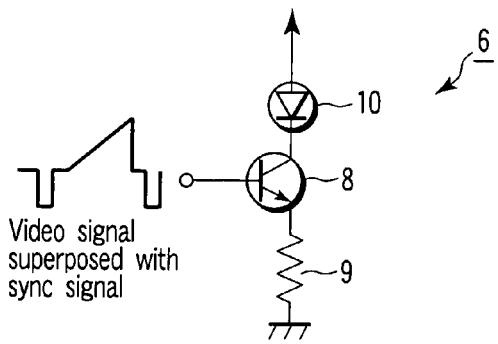
FIG. 2 is a diagram showing the configuration of the light emitting unit of the electronic endoscope apparatus, which includes an LED used as light emitting element.

FIG. 2 is a diagram showing the light emitting unit 6, which includes an LED used as light emitting element. As FIG. 2 shows, the light emitting unit 6 comprises a transistor 8, a resistor 9, and an LED 10. A current according to the signal output from the sync signal superposing circuit 5 is input to the base of the transistor 8. The signal input from the sync signal superposing circuit 5 has been adjusted to such a level that the current linearly changes while flowing in the LED 10. A current flows in the LED 10 even if the current according to the lowest level of the signal from the sync signal superposing circuit 5 has been supplied to the base of the transistor 8. This is because the transistor 8 should not operate unless its base-emitter voltage is equal to or higher than the value determined by its characteristics and the signal input from the sync signal superposing circuit 5 should be of such a value that the LED 10 emits light that linearly changes in amount.

Figure 3A:
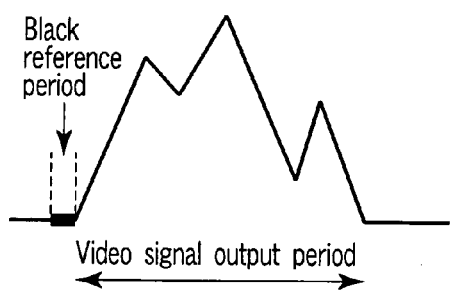
FIG. 3A is a diagram representing the waveform of a video signal sampled in the CDS circuit provided in the electronic endoscope apparatus.
Figure 3B:
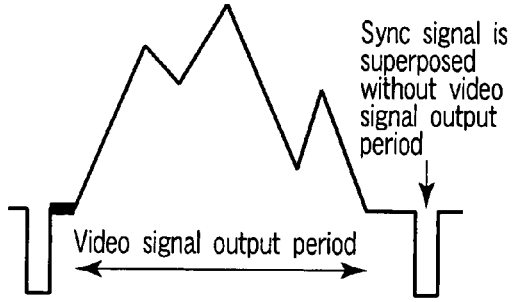
FIG. 3B is a diagram representing the waveform of a signal generated by superposing a sync signal on the video signal shown in FIG. 3A.

The timing of superposing the sync signal on the video signal in the sync signal superposing circuit 5 will be explained. FIG. 3A is a diagram representing the waveform of a video signal sampled in the CDS circuit 4. As shown in FIG. 3B, the sync signal that differs in polarity from the video signal is superposed on the video signal shown in FIG. 3A without a video signal output period. However, the sync signal is not superposed during the black reference period of the video signal, which is shown in FIG. 3A. This is because a clamping circuit 14, which will be described later, performs its function during the black reference period. Note that FIG. 3B pertains to the case where a horizontal sync signal is superposed on the video signal. In practice, a vertical sync signal having a larger pulse width than the horizontal sync signal is superposed on the video signal, too. The horizontal sync signal demarcates one-line sections of image from one another. The vertical sync signal demarcates one-frame sections of image from one another.

Figure 4:
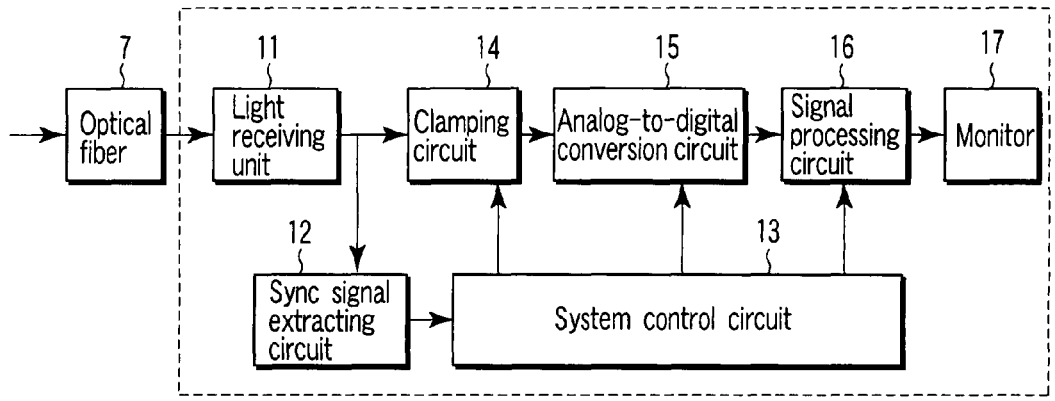
FIG. 4 is a block diagram showing the configuration of the external apparatus incorporated in the electronic endoscope system according to the first embodiment of the invention.

FIG. 4 is a block diagram that shows the configuration of the external apparatus incorporated in the electronic endoscope system according to the first embodiment. As shown in FIG. 4, the external apparatus comprises a light receiving unit 11, a sync signal extracting circuit 12, a system control circuit 13, a clamping circuit 14, an analog-to-digital conversion circuit 15, a signal processing circuit 16, and a monitor 17.

The light receiving unit 11 includes a light receiving element such as a photodiode. The unit 11 receives an optical signal supplied from the electronic endoscope apparatus through the optical fiber 7 and converts the optical signal into an electrical signal (video signal) that corresponds to the magnitude of the optical signal. The electrical signal is supplied to the sync signal extracting circuit 12 and the clamping circuit 14. The sync signal extracting circuit 12 extracts the sync signal from the output signal of the light receiving unit 11. The sync signal thus extracted is input to the system control circuit 13. From the sync signal, the system control circuit 13 generates clamping pulses and two clock signals. The clamping pulses are supplied to the clamping circuit 14. The first clock signal is supplied to the analog-to-digital conversion circuit 15. The second clock signal is supplied to the signal processing circuit 16. The clamping pulses indicate the timing at which the clamping circuit 14 should clamp the video signal. The first clock signal indicates the timing at which the analog-to-digital conversion circuit 15 should perform analog-to-digital conversion. The second clock signal indicates the timing at which the signal processing circuit 16 should process the video signal. The system control circuit 13 incorporates a PLL circuit (not shown). The PLL circuit synchronizes the clock signal input to the circuit 13, at the edges of the sync signal. The video signal, the analog-to-digital conversion clock signal and the image processing clock signal are thereby set in phase.

The clamping circuit 14 receives the clamping pulses from the system control circuit 13. Using these pulses, the clamping circuit 14 clamps the video signal coming from the light receiving unit 11 at such a voltage that the video signal may be readily undergo analog-to-digital conversion. The analog-to-digital conversion circuit 15 receives the clock signal supplied from the system control circuit 13. Using the clock signal, the analog-to-digital conversion circuit 15 converts that amplitude part of the video signal clamped, which corresponds to the image, into a digital signal. The signal processing circuit 16 processes the video signal on the basis of the clock signal and the sync signal, both supplied from the system control circuit 13. The monitor 17 displays the image represented by the video signal the signal processing circuit 16 has processed.

Configured as shown in FIG. 4, the external apparatus converts the optical analog signal supplied through the optical fiber 7, into an electrical signal. The electrical signal, or video signal, can therefore be supplied to the monitor 17.

Figure 5:
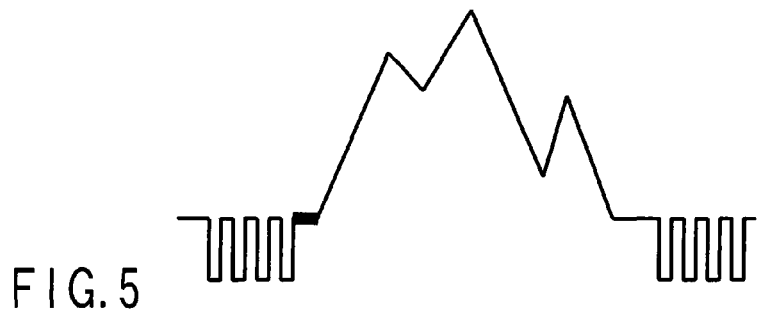
FIG. 5 is a diagram representing the waveform of a signal generated by superposing a clock signal on a video signal.

In the first embodiment, the sync signal is one pulse. However, the sync signal may be a clock signal having the same frequency as sampling pulses for pixels, and this clock signal may be superposed on the video signal as is illustrated in FIG. 5. If such a clock signal is superposed on the video signal, it is possible to shorten the time that the PLL circuit needs to determine a phase for the video signal, the analog-to-digital conversion clock signal and the image processing clock signal. This can enhance the phase precision. If the transmission bandwidth is narrow, a clock signal obtained by dividing the frequency of the sampling signal may be superposed on the video signal.

As described above, only one line, i.e., optical fiber, is required other than the power supply line in the first embodiment. This simplifies the distal part of the electronic endoscope apparatus in terms of configuration and can ultimately reduce the diameter of the electronic endoscope apparatus.

In the first embodiment, the video signal is transmitted, as an optical signal, through one optical fiber. The video signal is never affected by noise outside the optical fiber.

Second Embodiment

Figure 6:
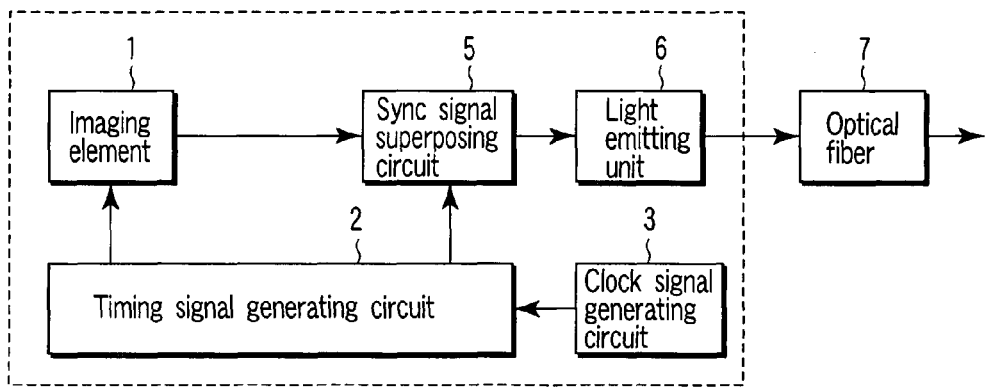
FIG. 6 is a block diagram showing the configuration of the electronic endoscope apparatus incorporated in an electronic endoscope system according to a second embodiment of the present invention.

A second embodiment of the present invention will be described. FIG. 6 is a block diagram that shows the configuration of the electronic endoscope apparatus incorporated in an electronic endoscope system according to the second embodiment. As seen from FIG. 6, the electronic endoscope apparatus according to the second embodiment differs from the one according to the first embodiment in that no component equivalent to the CDS circuit 4 is provided in the distal part. Hence, the circuit configuration of the distal part of the electronic endoscope apparatus can be smaller by the space the CDS circuit would occupy, than the electronic endoscope apparatus according to the first embodiment.

In the electronic endoscope apparatus thus configured, the imaging element 1 converts the light reflected from the body cavity of the subject, into an electrical signal (i.e., a video signal) the magnitude of which corresponds to the amount of the light. The electrical signal is output to the sync signal superposing circuit 5 connected to the output of the imaging element 1. The timing signal generating circuit 2 receives the clock signal coming from the clock signal generating circuit 3 and generates drive pulses that will drive the imaging element 1. The sync signal superposing circuit 5 superposes a sync signal on the video signal output from the imaging element 1 so that the external apparatus may reproduce the image. The light emitting unit 6 converts the video signal superposed with the sync signal in the sync signal superposing circuit 5, into an optical signal. The optical signal thus obtained is transmitted to the external apparatus through the optical fiber 7.

FIG. 7 is a block diagram showing the configuration of the external apparatus incorporated in the electronic endoscope system according to the second embodiment of the invention. As FIG. 7 shows, the external apparatus according to the second embodiment differs from the one according to the first embodiment in that it incorporates a CDS circuit 4.

In this external apparatus, the light receiving unit 11 receives an optical signal transmitted from the electronic endoscope apparatus through the optical fiber 7. The unit 11 converts the optical signal into an electrical signal, or a video signal corresponding to the amount of light. The video signal is output to the sync signal extracting circuit 12 and the CDS circuit 4. The sync signal extracting circuit 12 extracts the sync signal component of the output signal coming from the light receiving unit 11 and inputs the sync signal component to the system control circuit 13. The system control circuit 13 generates sampling pulses, clamping pulses, an analog-to-digital conversion clock signal and an image processing clock signal from the sync signal. The sampling pulses are supplied to the CDS circuit 4. The clamping pulses are supplied to the clamping circuit 14. The analog-to-digital conversion clock signal is supplied to the analog-to-digital conversion circuit 15. The image processing clock signal is supplied to the signal processing circuit 16. The system control circuit 13 incorporates a PLL circuit (not shown). The PLL circuit synchronizes the clock signal at the edges of the sync signal input to the system control circuit 13. The video signal, the analog-to-digital conversion clock signal and the image processing clock signal are thereby set in phase.

The CDS circuit 4 receives the sampling pulses from the system control circuit 13 and performs sampling on the video signal coming from the light receiving unit 11. The clamping circuit 14 receives the clamping pulses from the system control circuit 13 and clamps the video signal supplied from the CDS circuit 4. The analog-to-digital conversion circuit 15 receives the clock signal from the system control circuit 13. Using the clock signal, the analog-to-digital conversion circuit 15 converts that amplitude part of the video signal clamped, which corresponds to the image, into a digital signal. The signal processing circuit 16 processes the video signal on the basis of the clock signal and the sync signal, both supplied from the system control circuit 13. The monitor 17 displays the image represented by the video signal the signal processing circuit 16 has processed.

As described above, the CDS circuit 4 is provided in the external apparatus, not in the electronic endoscope apparatus, in the second embodiment. Hence, the distal part of the electronic endoscope apparatus can be made even smaller, while having the same advantages as the electronic endoscope apparatus according to the first embodiment.

Third Embodiment

A third embodiment of the present invention will be described. FIG. 8 is a block diagram that shows the configuration of the electronic endoscope apparatus incorporated in an electronic endoscope system according to the third embodiment. As seen from FIG. 8, the electronic endoscope apparatus according to the third embodiment is configured to transmit not only a video signal, but also another type of a signal, without increasing the number of lines. In the third embodiment, a video signal and a sync signal are transmitted from the electronic endoscope apparatus to the external apparatus.

As shown in FIG. 8, the electronic endoscope apparatus according to the third embodiment differs from those according to the first and second embodiments in that no component equivalent to the sync signal superposing circuit 5 is not provided and that a light emitting unit 18 is provided in addition to the light emitting unit 6 that converts a video signal into an optical signal.

The light reflected from a body cavity of the subject is applied to the distal part of the electronic endoscope apparatus. The imaging element 1 receives the light and converts it into an electrical signal (i.e., a video signal), which is output to the CDS circuit 4. The timing signal generating circuit 2 receives a clock signal from the clock signal generating circuit 3 and generates drive pulses and sampling pulses for driving the imaging element 1. The drive pulses are supplied to the imaging element 1, driving the imaging element 1. The sampling pulses are supplied to the CDS circuit 4, designating sampling timing for the CDS circuit 4. The CDS circuit 4 samples the video signal coming from the imaging element 1, in synchronism with the sampling pulses supplied from the timing signal generating circuit 2. The light emitting unit 6 receives the video signal from the CDS circuit 4 and converts it into an optical signal. The optical signal, which is a baseband signal, is transmitted to the external apparatus through the optical fiber 7.

The timing signal generating circuit 2 generates a sync signal that will be used to display the image in the external apparatus. The sync signal is output to the light emitting unit 18. The light emitting unit 18 converts the sync signal into an optical signal, which is transmitted to the external apparatus through the optical fiber 7. The optical signal output from the light emitting unit 18 are made different in wavelength from the optical signal output from the light emitting unit 6. To this end, the light emitting unit 18 may have an LED that differs in material from the LED of the light emitting unit 6. Since the optical signal for transmitting the video signal and the optical signal for transmitting the sync signal are difference in wavelength, they can be isolated from each other in the external apparatus.

The LED of the light emitting unit 6 and the LED of the light emitting unit 18 shown in FIG. 8 may be unitized in a single package. If this is the case, the electronic endoscope apparatus can be still smaller.

FIGS. 9A and 9B are diagrams illustrating the relationship between the sync signal and the video signal. More precisely, FIG. 9A is a diagram representing the waveform of a sync signal. The sync signal is a vertical sync signal indicating the head of a frame and inserted in a clock signal. The clock signal, which is part of the sync signal, performs the same function as shown in FIG. 5. The vertical sync signal shown in FIG. 9A only needs to have a pattern that can be distinguished from the clock signal. The vertical sync signal may differ in, for example, frequency from the clock signal. Alternatively, the vertical sync signal may not have a periodic pattern, but a pattern in that is irregular in terms of high and low levels. For example, the vertical sync signal may be a non-periodic pattern such as 1110010001 if the clock signal has a pattern of 1010101010.

The vertical sync signal is followed by a period in which a clock signal is output. In this period of outputting the clock signal, such an analog baseband video signal as shown in FIG. 9B is transmitted in the form of an optical signal that differs in wavelength from the clock signal. Such a horizontal sync signal as shown in FIG. 9A is inserted at the end of the clock signal for a one-line image. The pattern selected for the horizontal sync signal is different from that of the vertical sync signal and that of the clock signal. The horizontal sync signals are inserted at the boundaries between the one-line segments of the video signal, respectively. The vertical sync signal is inserted at the boundary between any two adjacent one-frame segments of the video signal. The external apparatus detects the patterns of any sync signal it has received, thereby reproducing the sync signal.

FIG. 10 is a block diagram showing the configuration of the external apparatus incorporated in the electronic endoscope system according to the third embodiment of the invention. As FIG. 10 shows, the external apparatus differs from that of the first and second embodiments in that a spectral filter 19 and a light receiving unit 20 are provided. Note that the light receiving unit 20 is provided corresponding to the light emitting unit 18.

The spectral filter 19, which is used as a light extracting unit, extracts the optical signal supplied through the optical fiber 7 and guides the extracted optical signal to the light receiving units 11 and 20. The spectral filter 19 will be described with reference to FIG. 11. The spectral filter 19 incorporates two mirrors 19a that pass or reflect light in accordance with the wavelength of the light. Assume that mirrors 19a shown in FIG. 11 allow passage of light having wavelength of 640 nm and reflect light having wavelength of 550 nm, and that the wavelength of the optical video signal is set to 640 nm while the wavelength of the optical sync signal is set at 550 nm. Then, the mirrors 19a allow passage of the optical video signal and reflect the optical sync signal. Since the mirrors 19a work in this way, the spectral filter 19 divides the multiplexed light transmitted to the external apparatus, into two light beams. These light beams are guided to the light receiving units 11 and 20, respectively.

The light receiving unit 20 receives the optical signal reflected in the spectral filter 19 and converts the same into an electrical signal (sync signal). The sync signal is input to the system control circuit 13. From the sync signal the system control circuit 13 generates clamping pulses, an analog-to-digital conversion clock signal and an image processing clock signal. The clamping pulses are output to the clamping circuit 14. The analog-to-digital conversion clock signal is output to the analog-to-digital conversion circuit 15. The image processing clock signal is output to the signal processing circuit 16.

The light receiving unit 11 receives the optical signal coming from the spectral filter 19 and converts the same into an electrical signal (video signal) that corresponds to the magnitude of the optical signal. The video signal is output to the clamping circuit 14. Using the clamping pulses coming from the system control circuit 13, the clamping circuit 14 clamps the video signal coming from the light receiving unit 11. The analog-to-digital conversion circuit 15 receives the clock signal from the system control circuit 13. Using this clock signal, the analog-to-digital conversion circuit 15 converts that amplitude part of the video signal clamped, which corresponds to the image, into a digital signal. The signal processing circuit 16 processes the video signal on the basis of the clock signal and the sync signal, both supplied from the system control circuit 13. The monitor 17 displays the image represented by the video signal the signal processing circuit 16 has processed.

As described above, a video signal and a sync signal can be multiplexed into one signal, which is transmitted through one optical fiber in the third embodiment. Hence, the electronic endoscope apparatus need not have a component equivalent to the sync signal superposing circuit 5. The unit for providing the multiplexed signal uses only two light emitting units (i.e., LEDs) that emit light beams of different wavelengths. Therefore, the distal part of the electronic endoscope apparatus can be smaller than in the first embodiment.

In the third embodiment, the CDS circuit 4 may be provided in the external apparatus as in the second embodiment.

Fourth Embodiment

Figure 12:
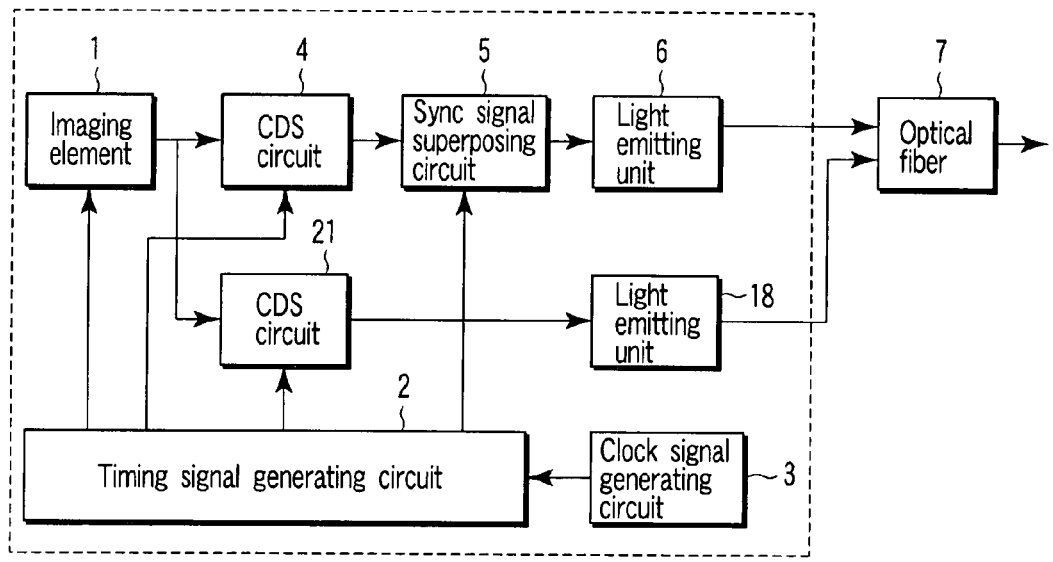
FIG. 12 is a block diagram showing the configuration of the electronic endoscope apparatus incorporated in an electronic endoscope system according to a fourth embodiment of the present invention.

A fourth embodiment of the present invention will be described. FIG. 12 is a block diagram that shows the configuration of the electronic endoscope apparatus incorporated in an electronic endoscope system according to the fourth embodiment. In the fourth embodiment, the video signal is multiplexed. The fourth embodiment differs from the third embodiment in that, as shown in FIG. 12, two CDS circuits 4 and 21 are provided to sample a video signal supplied from the imaging element 1.

The imaging element 1 receives the light reflected from the body cavity of the subject, into an electrical signal (i.e., a video signal). The electrical signal is output to the CDS circuits 4 and 21, both connected to the output of the imaging element 1. The fourth embodiment, the CDS circuits 4 and 21 sample different color components, respectively. The imaging element 1 may be one having red, green and blue color filters of the Bayer arrangement. If this is the case, the CDS circuit 4 samples the green component only and outputs the same to the sync signal superposing circuit 5, and the CDS circuit 21 samples the red component and the blue component alternately, line by line, and output the red components and the blue components to the light emitting unit 18.

Figure 13:
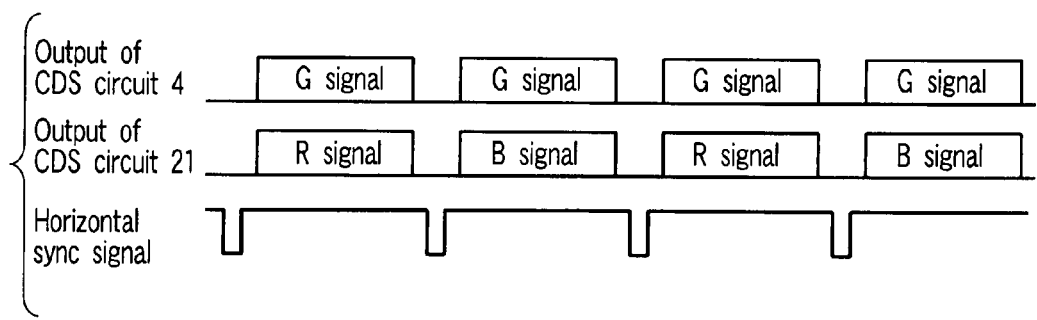
FIG. 13 is a diagram explaining the sampling performed in the CDS circuits 4 and 21 that are incorporated in the electronic endoscope apparatus shown in FIG. 12.

FIG. 13 is a diagram explaining the sampling performed in the CDS circuits 4 and 21. The imaging element 1 outputs a green (G) signal and red (R) signal alternately during each odd-numbered horizontal period, and outputs a blue (B) signal and green (G) signal alternately during each even-numbered horizontal period. Therefore, the CDS circuit 4 and the CDS circuit 21 alternately perform sampling, clock pulse by clock pulse. Nonetheless, the CDS circuits 4 and 21 operate in one order during the horizontal period and in the reverse order during the vertical period. Since the sampling is performed in this manner, the CDS circuit 4 outputs only a G signal, while the CDS circuit 21 outputs R and B signals alternately.

The timing signal generating circuit 2 receives a clock signal from the clock signal generating circuit 3 and generates drive pulses and sampling pulses. The drive pulses are supplied to the imaging element 1, driving the imaging element 1. The sampling pulses are supplied to the CDS circuits 4 and 21, driving these circuits. The sync signal superposing circuit 5 superposes a sync signal on the video signal output from the CDS circuit 4 so that the external apparatus may reproduce the image. The sync signal superposing circuit 5 may be provided at the output of the CDS circuit 21.

The light emitting unit 6 converts the video signal supplied from the sync signal superposing circuit 5, into a baseband optical signal. This optical signal thus obtained is transmitted to the external apparatus through the optical fiber 7. The light emitting unit 18 receives the video signal (i.e., R and B signals) coming from the CDS circuit 21 and converts them into an optical signal. The optical signal is transmitted through the optical fiber 7 to the external apparatus. In the fourth embodiment, the optical signals output from the light emitting units 6 and 18 may be set to different wavelengths as in the third embodiment.

Figure 14:
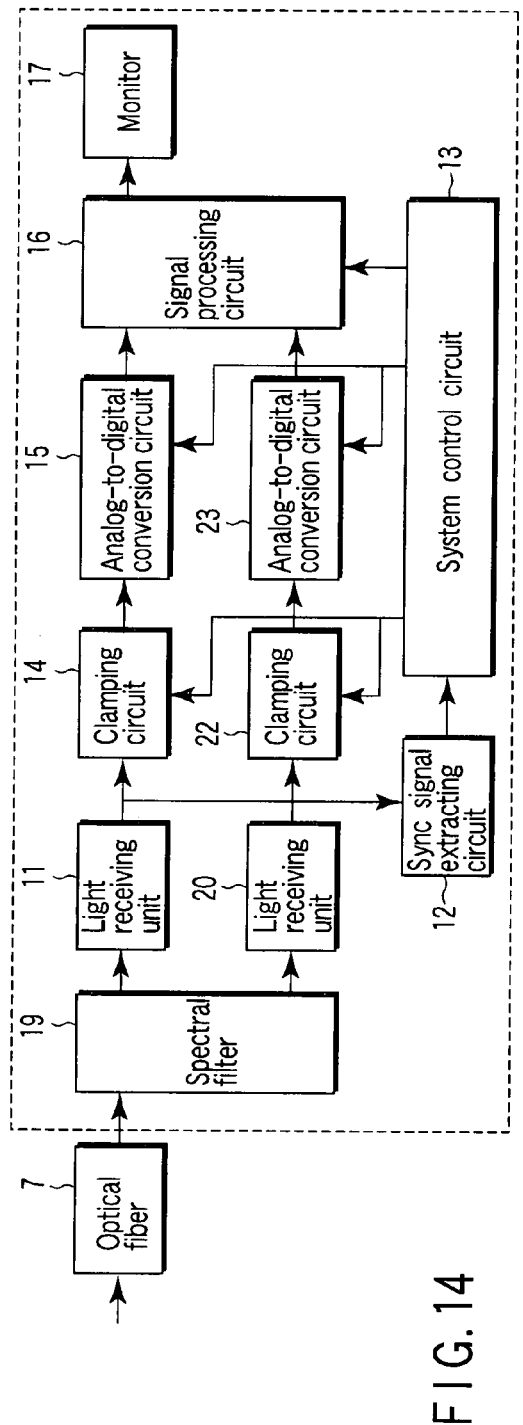
FIG. 14 is a block diagram showing the configuration of the external apparatus incorporated in the electronic endoscope system according to the fourth embodiment of the invention.

FIG. 14 is a block diagram showing the configuration of the external apparatus incorporated in the electronic endoscope system according to the fourth embodiment of this invention. The external apparatus differs from that of any other embodiment described above in that, as shown in FIG. 14, two light receiving units, two clamping circuits and two analog-to-digital conversion circuits are provided to process two types of video signals.

The spectral filter 19 receives the optical signal applied through the optical fiber 7 and divides the signal into two light beams, which are applied to the light receiving units 11 and 20. Note that the spectral filter 19 has the same configuration as has been described in conjunction with the third embodiment.

The light receiving unit 11 receives the optical signal that has passed through the spectral filter 19 and convert the light into an electrical signal (G signal, i.e., a video signal) the magnitude of which corresponds to the optical signal. The video signal is output to the clamping circuit 14. Using the clamping pulses coming from the system control circuit 13, the clamping circuit 14 clamps the video signal coming from the light receiving unit 11. The analog-to-digital conversion circuit 15 receives the clock signal from the system control circuit 13. Using this clock signal, the analog-to-digital conversion circuit 15 converts that amplitude part of the video signal clamped, which corresponds to the image, into a digital signal.

The light receiving unit 20 receives the optical signal reflected by the spectral filter 19 and converts this light into an electrical signal (R and B signals, i.e., a video signal). The video signal is output to the clamping circuit 22. Using the clamping pulses received from the system control circuit 13, the clamping circuit 22 clamps the video signal supplied from the light receiving unit 20. Using the clock signal from the system control circuit 13, the analog-to-digital conversion circuit 23 converts that amplitude part of the video signal clamped, which corresponds to the image, into a digital signal.

The signal processing circuit 16 processes the signals output from the analog-to-digital conversion circuits 15 and 23, rearranging these signals so that the arrangement of the color components becomes the Bayer arrangement. The circuit 16 further processes the signals so that the monitor 17 may display well the image represented by these signals. The signals so processed are output to the monitor 17. The monitor 17 displays the image represented by the video signals the signal processing circuit 16 has processed.

As in any other embodiment described above, the sync signal extracting circuit 12 extracts a sync signal from the signal output from the light receiving unit 11 and input to the system control circuit 13. The system control circuit 13 incorporates a PLL circuit, which synchronizes the clock signal at the edges of the sync signal input. The video signal and the analog-to-digital conversion clock signal are thereby set in phase.

As described above, the video signal is divided into two signals and these signals are transmitted independently in the fourth embodiment. The transmission frequency can therefore be reduced to ½. This is a useful means for lowering the frequency in the case where the transmission frequency is limited in a system that handles video data representing a great number of pixels.

In the fourth embodiment, a sync signal may be multiplexed, too, and then transmitted, as in the third embodiment. If this is the case, however, LEDs that emit light beams of different wavelengths must be used in the same numbers as the optical signals that should be multiplexed.

Fifth Embodiment

Figure 15:
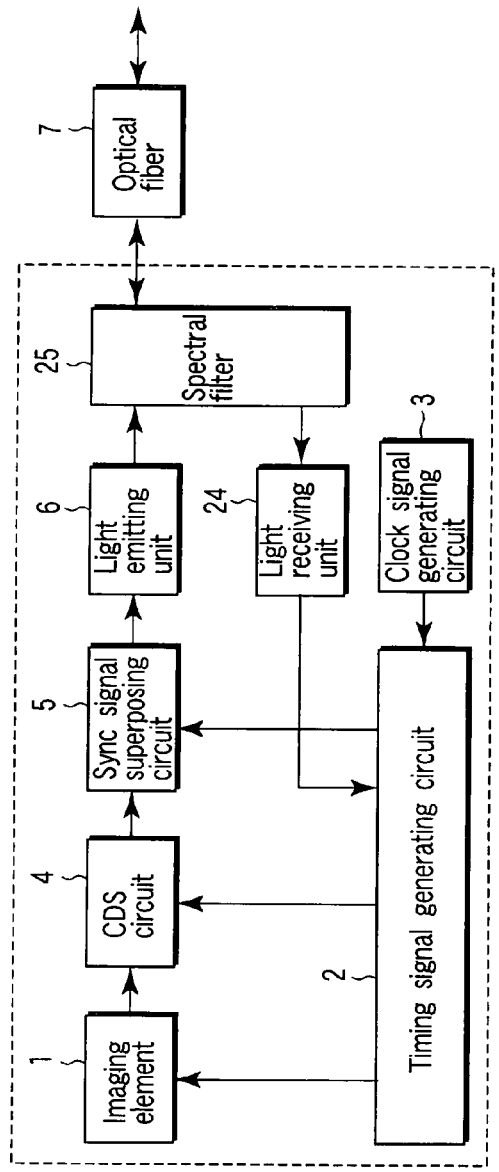
FIG. 15 is a block diagram showing the configuration of the electronic endoscope apparatus incorporated in an electronic endoscope system according to a fifth embodiment of the present invention.

A fifth embodiment of the present invention will be described. FIG. 15 is a block diagram that shows the configuration of the electronic endoscope apparatus incorporated in an electronic endoscope system according to the fifth embodiment. In the fifth embodiment, the signals are multiplexed by a method different from the method used in the third and fourth embodiments, in order to accomplish bidirectional communication. As seen from FIG. 15, the fifth embodiment differs from the third and fourth embodiments in that a light receiving unit 24 and a spectral filter 25 are provided.

The imaging element 1 receives the light reflected from the body cavity of the subject, into an electrical signal (i.e., a video signal). The electrical signal is output to the CDS circuit 4 connected to the output of the imaging element 1. The timing signal generating circuit 2 receives a clock signal from the clock signal generating circuit 3 and generates drive pulses and sampling pulses. The drive pulses are supplied to the imaging element 1, driving the imaging element 1. The sampling pulses are supplied to the CDS circuit 4, driving the CDS circuit 4. The CDS circuit 4 samples the video signal coming from the imaging element 1, in synchronism with the sampling pulses supplied from the timing signal generating circuit 2. The output of the CDS circuit 4 is input to the sync signal superposing circuit 5. The sync signal superposing circuit 5 superposes a sync signal on the video signal output from the CDS circuit 4 so that the external apparatus may reproduce the image. The light emitting unit 6 converts the video signal superposed with the sync signal in the sync signal superposing circuit 5, into an optical signal. This optical signal thus obtained is transmitted to the optical fiber 7 through the spectral filter 25.

Figure 11:
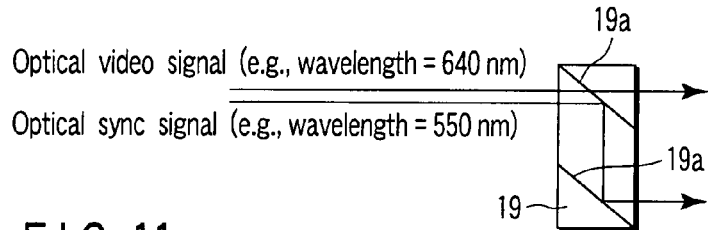
FIG. 11 is a diagram showing the configuration of the spectral filter 19 provided in the external apparatus shown in FIG. 10.
Figure 16:
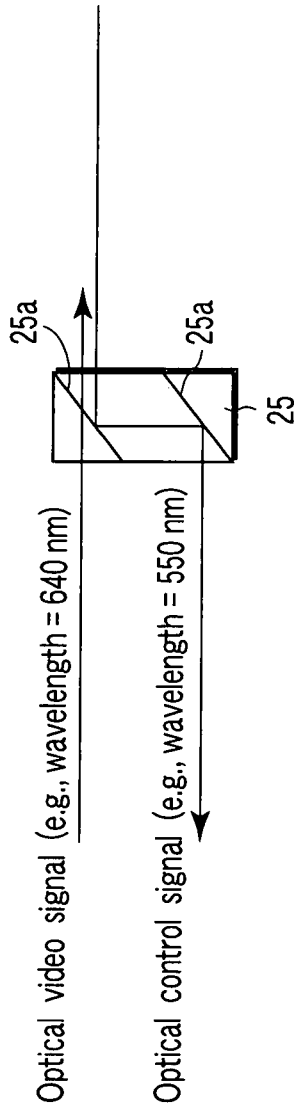
FIG. 16 is a diagram showing the configuration of the spectral filter 25 provided in the external apparatus shown in FIG. 15.

The spectral filter 25 operates in the same way as has been explained with reference to FIG. 11 in conjunction with the third embodiment. In the fifth embodiment, however, the two light beams of different wavelengths are applied to the filter 25 in different directions, not in the same direction as is illustrated in FIG. 11. FIG. 16 is a diagram showing the configuration of the spectral filter provided 25. In the left part of FIG. 16, the light emitting unit 6 and the light receiving unit 24 are arranged as shown in FIG. 15. The output of the light emitting unit 6 is, for example, an optical signal having wavelength of 640 nm. This optical signal is applied from the left to the spectral filter 25. In this case, the optical signal passes through the mirror 25a and is guided to the right, or to the optical fiber 7. Meanwhile, a light beam having wavelength of 550 nm is applied from the external apparatus, or from the right, to the spectral filter 25 through the optical fiber 7. The mirror 25a reflects this optical signal, which is guided to the left, or to the light receiving unit 24 not shown in FIG. 16. The light receiving unit 24 converts the optical signal coming from the external apparatus via the spectral filter 25, into an electrical signal. The electrical signal is input to the timing signal generating circuit 2. The signal supplied transmitted from the external apparatus is a control signal for changing, for example, the frame rate at which the imaging element 1 is driven. In the present embodiment, the spectral filter 25 is arranged in the distal part of the electronic endoscope apparatus. Nevertheless, the spectral filter 25 need not be provided in the distal part if the light receiving unit 24 is configured to receive light of a specified wavelength only.

Figure 17:
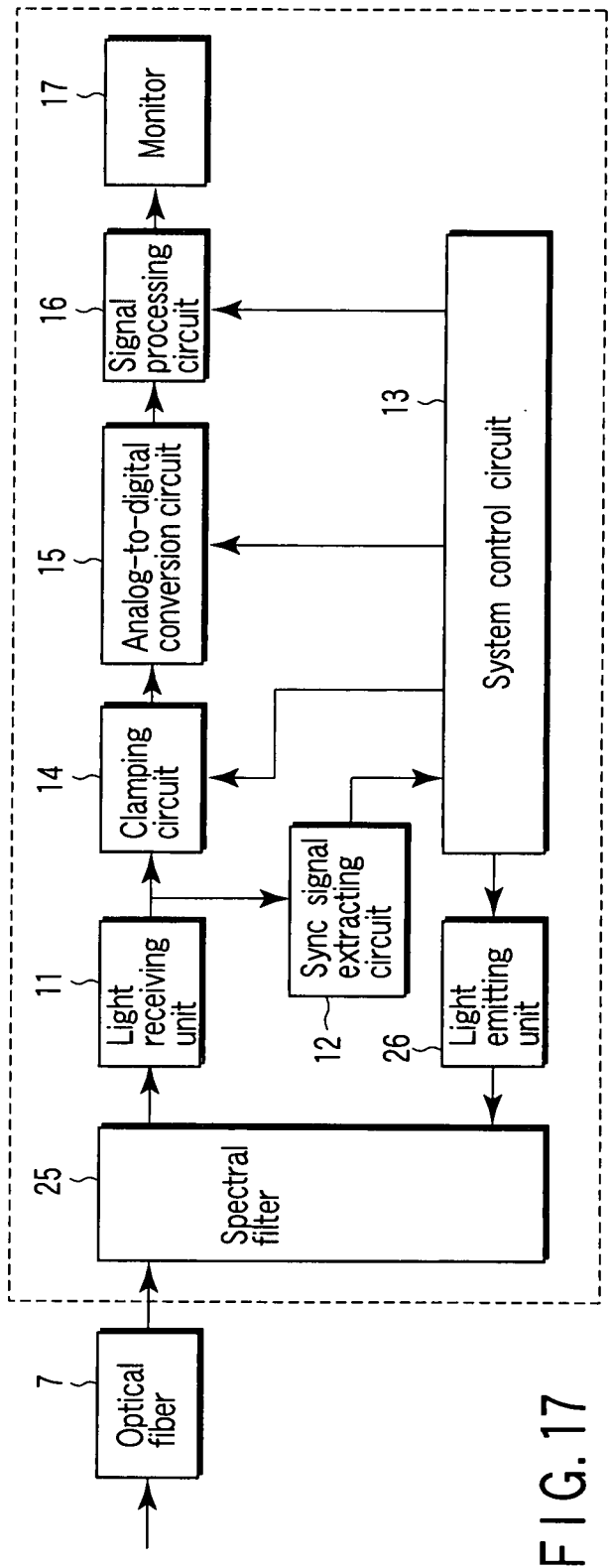
FIG. 17 is a block diagram showing the configuration of the external apparatus incorporated in the electronic endoscope system according to the fifth embodiment of the invention.

FIG. 17 is a block diagram showing the configuration of the external apparatus incorporated in the electronic endoscope system according to the fifth embodiment. The external apparatus according to the fifth embodiment differs from that of any other embodiment, in that a spectral filter 25 and a light emitting unit 26, both identical in structure to their counterparts shown in FIG. 15.

The light receiving unit 11 receives an optical signal transmitted from the electronic endoscope apparatus through the optical fiber 7 and converts the same into an electrical signal (video signal) that corresponds to the magnitude of the optical signal. The electrical signal is output to the sync signal extracting circuit 12 and the clamping circuit 14. The sync signal extracting circuit 12 extracts a sync signal component from the output signal of the light receiving unit 11. The sync signal thus extracted is input to the system control circuit 13. From the sync signal the system control circuit 13 generates clamping pulses, an analog-to-digital conversion clock signal and an image processing clock signal. The clamping pulses are output to the clamping circuit 14. The analog-to-digital conversion clock signal is output to the analog-to-digital conversion circuit 15. The image processing clock signal is output to the signal processing circuit 16. The system control circuit 13 incorporates a PLL circuit (not shown). The PLL circuit synchronizes the clock signal input to the circuit 13, at the edges of the sync signal. The video signal, the analog-to-digital conversion clock signal and the image processing clock signal are thereby set in phase.

Using the clamping pulses supplied from the system control circuit 13, the clamping circuit 14 clamps the video signal coming from the light receiving unit 11, thus converting the video signal into a voltage that can be readily undergo analog-to-digital conversion. The analog-to-digital conversion circuit 15 receives the clock signal supplied from the system control circuit 13. Using the clock signal, the analog-to-digital conversion circuit 15 converts that amplitude part of the video signal clamped, which corresponds to the image, into a digital signal. The signal processing circuit 16 processes the video signal on the basis of the clock signal and the sync signal, both supplied from the system control circuit 13. The monitor 17 displays the image represented by the video signal the signal processing circuit 16 has processed.

In the fifth embodiment, the imaging element 1 can be driven under the control of the system control circuit 13. To change the mode of driving the imaging element 1, the system control circuit 13 outputs a control signal to the light emitting unit 26. The light emitting unit 26 converts the control signal into an optical signal that differs in wavelength from the video signal. This optical signal is supplied to the optical fiber 7 via the spectral filter 25.

As described above, the video signal and the control signal for controlling the imaging element can be transmitted through one optical fiber in the fifth embodiment. This can reduce the diameter of the electronic endoscope apparatus.

In the fifth embodiment, too, the sync signals may be multiplexed as in the third embodiment, and the color signal may be transmitted in two components as in the fourth embodiment. If this is the case, however, LEDs that emit light beams of different wavelengths must be used in the same numbers as the optical signals that should be multiplexed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An electronic endoscope apparatus comprising:
a distal part;
an imaging unit which is provided in the distal part and configured to convert light applied to the distal part, into an electrical signal;
a sync signal superposing unit which is configured to superpose a sync signal on the electrical signal in order to reproduce the electrical signal;
a light emitting unit which is configured to convert a signal output from the sync signal superposing unit, into an optical signal; and
a transmitting unit which is attached to the distal part and configured to guide the optical signal from the light emitting unit,
wherein the optical signal is transmitted from the distal part through the transmitting unit.

2. An electronic endoscope apparatus comprising:
a distal part;
an imaging unit which is provided in the distal part and configured to convert light applied to the distal part, into an electrical signal;
a sampling unit which is configured to sample the electrical signal supplied from the imaging unit;
a sync signal superposing unit which is configured to superpose a sync signal on a signal output from the sampling unit in order to reproduce an image;
a light emitting unit which is configured to convert a signal output from the sync signal superposing unit, into an optical signal; and
a transmitting unit which is attached to the distal part and configured to guide the optical signal from the light emitting unit,
wherein a baseband electrical signal supplied from the sync signal superposing unit is converted into an optical signal, and the optical signal is transmitted from the distal part through the transmitting unit.

3. An electronic endoscope system comprising:
an electronic endoscope apparatus including:
an imaging unit which is configured to convert light into an electrical signal;
a sync signal superposing unit which is configured to superpose a sync signal on the electrical signal in order to reproduce the electrical signal;
a light emitting unit which is configured to convert a signal output from the sync signal superposing unit, into an optical signal; and
a transmitting unit which is configured to guide the optical signal from the light emitting unit, and
an external apparatus including:
a light receiving unit which is configured to convert the optical signal guided by the transmitting unit, into an electrical signal;
a sync signal extracting unit which is configured to extract the sync signal from the electrical signal supplied from the light receiving unit;
a control unit which is configured to generate a control signal for controlling any other component of the external apparatus; and
a signal processing unit which is configured to process the electrical signal supplied from the light receiving unit,
wherein a baseband electrical signal supplied from the sync signal superposing unit is converted into an optical signal, and the optical signal is transmitted from the distal part through the transmitting unit.

4. The electronic endoscope system according to claim 3, wherein the sync signal superposing unit superposes a clock signal on the sync signal when the sync signal is superposed on the signal output from the sampling unit, and the control unit generates sampling pulses from the clock signal superposed on the sync signal in order to reproduce a color signal.

5. An electronic endoscope system comprising:
- an imaging unit which is configured to convert light into an electrical signal;
- a sync signal superposing unit which is configured to superpose a sync signal on the electrical signal in order to reproduce the electrical signal,
- a first light emitting unit which is configured to convert the electrical signal, into an optical signal;
- at least one second light emitting unit which is configured to convert data different from the data contained in the optical signal generated by the first light emitting unit, into an optical signal having a wavelength different from that of the optical signal generated by the first emitting unit;
- a transmitting unit which is configured to multiplex the optical signals supplied from the first light emitting unit and the said at least one second light emitting units;
- a light splitting unit which is configured to split the optical signal supplied from the transmitting unit, into the optical signal supplied from the first light emitting unit and the optical signal supplied from the at least one second light emitting unit;
- a first light receiving unit which is configured to convert an optical signal equivalent to the optical signal supplied first from the first light emitting and then from the light splitting unit, into an electrical signal;
- a second light receiving unit which is configured to convert an optical signal equivalent to the optical signal supplied first from the at least one second light emitting and then from the light splitting unit, into an electrical signal;
- a signal processing unit which is configured to process the electrical signal output from the first light receiving unit.

6. The electronic endoscope system according to claim 5, wherein the sync signal enables to display an image.

7. The electronic endoscope system according to claim 5, wherein data contained in the optical signal generated by the first light emitting unit is equivalent to a one-color electrical signal supplied from the imaging unit, and data contained in the optical signal generated by the at least one second light emitting unit is equivalent to an electrical signal pertaining to a plurality of color components which is different from the one-color electrical signal.

8. The electronic endoscope system according to claim 5, wherein the at least one second light emitting unit is provided in an external apparatus, and the second light receiving unit is provided in an electronic endoscope apparatus.

9. The electronic endoscope system according to claim 8, wherein the imaging unit is provided in the electronic endoscope apparatus, and data for controlling the imaging unit is transmitted from the at least one second light emitting unit.

* * * * *